United States Patent [19]
Fairleigh et al.

[11] Patent Number: 6,093,162
[45] Date of Patent: Jul. 25, 2000

[54] DYNAMIC SPLINT FOR POST-OPERATIVE TREATMENT OF FLEXIBLE IMPLANT ARTHROPLASTY OF THE FINGERS

[76] Inventors: Angela Fairleigh, 1147 West 8th Avenue, Vancouver, British Columbia, Canada, V6H 1C5; Eugene Duruisseau, 942 Garrow Drive, Port Moody, British Columbia, Canada, V3H 1H9

[21] Appl. No.: 09/192,377

[22] Filed: Nov. 16, 1998

[51] Int. Cl.[7] ................................................ A61F 5/00
[52] U.S. Cl. .................................................. 602/22; 602/5
[58] Field of Search ................................ 602/5, 16, 20, 602/21, 6, 7, 30; 128/877–880; 623/57, 63, 64; 601/33, 40; 482/44, 47, 49

[56] References Cited

U.S. PATENT DOCUMENTS

| | | |
|---|---|---|
| 897,471 | 9/1908 | Loyola ....................................... 482/48 |
| 4,456,002 | 6/1984 | Barber et al. . |
| 4,558,694 | 12/1985 | Barber . |
| 4,602,620 | 7/1986 | Marx . |
| 4,643,177 | 2/1987 | Sheppard et al. . |
| 4,677,971 | 7/1987 | Lindemann . |
| 4,719,906 | 1/1988 | DeProspero . |
| 4,765,320 | 8/1988 | Lindemann et al. . |
| 4,772,012 | 9/1988 | Chesher ..................................... 272/67 |
| 4,790,300 | 12/1988 | Marx . |
| 4,873,968 | 10/1989 | Finnieston et al. . |
| 4,949,711 | 8/1990 | Gyovai et al. . |
| 5,152,739 | 10/1992 | Grob ............................................. 602/5 |
| 5,191,903 | 3/1993 | Donohue .................................. 128/879 |
| 5,222,986 | 6/1993 | Wright ....................................... 623/64 |
| 5,230,699 | 7/1993 | Grasinger ................................. 602/22 |
| 5,303,696 | 4/1994 | Boice ........................................ 601/33 |
| 5,346,462 | 9/1994 | Barber ...................................... 602/22 |

OTHER PUBLICATIONS

McGraw et al., "Development of a Tubular Orthosis for the Post–operative Management of the Swanson's Mcp Arthroplasty #85–21", 1988 & Aug. 1993.

Orthopaedic Insight, vol. 1, No. 2, Jan. 1994, pp. 2–7.

Report to Vancouver Foundation, Mar., 1988.

Fairleigh et al., "Post–operative Metacarpophalangeal Arthroplasty Dynamic Splint for Patients with Rheumatoid Arthritis" (1988). Canadian Journal of Occupational Therapy 55 (3) 141–146.

*Primary Examiner*—Kim M. Lee
*Attorney, Agent, or Firm*—Oyen Wiggs Green & Mutala

[57] ABSTRACT

An improved splint for post-operative treatment of a patient following flexible implant arthroplasty of the fingers. The splint is sizeable to a patient's hand, and features controls for the degree of flexion and extension of each finger, as well as for the alignment of the splint with the natural pivot axis of the finger joint(s) which have been repaired.

25 Claims, 6 Drawing Sheets

DYNAMIC SPLINT FOR POST-OPERATIVE TREATMENT OF FLEXIBLE IMPLANT ARTHROPLASTY OF THE FINGERS

TECHNICAL FIELD

This application relates to an improved hand splint. The splint is particularly suited for the treatment of patients following flexible implant arthroplasty of the fingers.

BACKGROUND

The hands of patients suffering from rheumatoid or osteoarthritis are often deformed by the disease process. Deterioration of the metacarpophalangeal (MCP) joints may cause loss of range, ulnar drift and subluxation, resulting in pain and partial to total dysfunction of the fingers. These conditions can be treated surgically. Implant arthroplasty of the damaged joints involves the insertion of silicone implants which act as spacers between the bones of the reconstructed joint to maintain their internal alignment. Arthroplasty restores some degree of function to the damaged joints and helps alleviate joint pain.

Arthroplasty is most commonly used to reconstruct the MCP joints of arthritic patients. However, the same techniques may be used to repair the distal and proximal interphalangeal joints of the fingers and thumb. This type of MCP joint arthroplasty was pioneered by Dr. Alfred Swanson in the 1960s. The operation involves excision of the metacarpal heads and reaming of the intramedullary canals. A flexible silicone implant with titanium circumferential grommets is then inserted into the canals. Finally, the ligaments and tendons around the implant are reattached to achieve a balanced joint.

The use of splinting in the post-operative management of MCP joint arthroplasty is imperative to the success of the procedure. During recovery, the reconstructed joints must be supported to prevent stretching of reconstructed tendons and ligaments during tissue regeneration. Accordingly, the support should be firm enough to minimize any lateral movement of the fingers. At the same time, the splint should be dynamic enough to allow movement in the desired plane and range. As part of the post-operative regimen, the finger must be allowed to reciprocate between a flexed and an extended position, with the degree of flexion and extension increasing in the course of the regimen. Because the patient has an active role in the post-operative period, the design of the splint should be simple enough to encourage patient participation. The splint should also be as unobstructive as possible, and light enough to prevent fatigue.

In most prior art hand splints, the dynamic force required for finger extension is generated by springs or rubber bands attached to rigging which operates in conjunction with a dorsal outrigger structure. Such splints suffer from several serious drawbacks. Custom fabrication and fitting of outrigger splints is time-consuming (typically 4–8 hours per splint) and requires professional expertise. Moreover, such splints lose accuracy of fit due to exaggerated ulnar directed extension lift and cause resistance to flexion.

Several hand splints are the subject of granted patents. U.S. Pat. No. 4,602,620 discloses an outrigger splint with pulleys juxta-positioned to the fingers of the hand, mounted to the outrigger structure, and guiding a rigging line attached to a fixed-length spring. The dynamic force is controlled by the choice of a colour-coded spring used to anchor the rigging line.

U.S. Pat. No. 4,765,320 discloses an outrigger splint with an elongated, laterally adjustable rigging guide operating as a pulley for changing the direction and the force applied by a rigging. The dynamic force is controlled by an elastic band used to anchor the rigging line.

U.S. Pat. No. 4,949,711 discloses an outrigger splint which uses a single extensible coil spring to generate variable tension force in the rigging. The tension force is adjusted by the choice of attachment point for the coil spring securable on the base of the splint by use of releasable hook and loop fasteners.

U.S. Pat. No. 4,772,012 discloses a dynamic splint with a work arm tensioned by a torsion spring, and a band connected at one end to the work arm and at the other to a connecting member on the finger.

In all of these prior art examples, the dynamic force always pulls the fingers toward an extension position. Some devices allow control of the amount of the dynamic force exerted, either by interchanging the flexible elements which create the force, or by altering their anchorage position. No means is provided for training the fingers in a flexion or partial flexion position or ensuring that the joint will flex relative to a natural pivot axis.

The need has therefore arisen for a dynamic hand splint which overcomes the various shortcomings of the prior art. The applicant's splint described herein is pre-assembled for easier and faster fitting, is readily adjustable while being worn by the patient for optimum joint alignment, and does not apply radial or protractive/retractive forces to the joint during function which can interfere with post-operative tissue healing.

SUMMARY OF INVENTION

In accordance with the invention, a splint for post-operative treatment of a patient following flexible implant arthroplasty of the fingers is disclosed. The splint is primarily designed to allow function by controlling movement and assisting the extensor muscles following arthroplasty of the metacarpophalangeal joint, but may also be used following surgical replacement of the distal interphalangeal or proximal interphalangeal joints, or to control the thumb following MCP joint arthroplasty. The splint includes a brace securable to a limb of the patient, such as a forearm; a finger support for engaging at least one finger of the patient, wherein the finger support is moveable about a pivot axis to permit movement of the finger between extended and flexed positions; and an adjustment frame coupling the finger support to the brace for adjusting the position of the pivot axis until it intersects the finger joint. The splint thereby ensures that the axis of movement of the finger support is approximately aligned with the natural pivot axis of the finger joint in question.

Preferably the width, height and length of the adjustment frame are independently adjustable. The adjustment frame may be pivotally coupled to the brace to enable adjustment of the height and inclination of the pivot axis. More particularly, the adjustment frame may include a rod pivotally coupled to the brace and extending transversely between opposite sides of the splint; and at least one (and preferably a pair) of side frames slidably coupled to the rod for varying the width of the adjustment frame. The side frames are releasably lockable at a selected transverse position and extend upwardly and outwardly from the rod to a respective side of the splint. The adjustment frame may further include at least one side bar extending longitudinally, preferably alongside the patient's hand, which is sidably coupled to an upper end of a respective side frame and is lockable at a selected longitudinal position. The side bar may be adjusted to vary the longitudinal position of the pivot axis and the overall length of the splint.

The finger support is preferably pivotally coupled to a forward end of the adjustment frame, such as a forward end of a corresponding side bar. The finger support may be biased toward the extended position. A flexion lock is provided for releasably locking the finger support against the bias at a selected angular position between the extended and flexed positions. An adjustable stop for restraining rearward pivoting motion of the finger support in the extended position is also provided.

The finger support may consist of at least one rigging arm pivotally coupled to a side bar and extending inwardly therefrom above a finger of the patient in the extended position, and a sling adjustably connectable to the rigging arm for supporting the patient's finger. The finger support may further include a spar sliding transversely on the rigging arm and lockable at a selected transverse position, the spar having a support rod which extends longitudinally; and a sling holder sidable longitudinally on the spar. The sling is detachably connectable to the spar. Preferably each finger support comprises a pair of rigging arms independently pivotable relative to a side bar, wherein the rigging arms extend at different elevations above the fingers of the patient in the extended position. The splint is ordinarily configured so that it includes a pair of finger supports pivotally coupled on opposite sides of the adjustment frame.

BRIEF DESCRIPTION OF DRAWINGS

In drawings which illustrate the preferred embodiment of the invention, but which should not be construed as restricting the spirit or scope of the invention in any way.

DESCRIPTION OF THE PREFERRED EMBODIMENT

This application relates to a hand splint 10 for the postoperative treatment of flexible implant arthroplasty of the fingers, principally metacarpophalangeal joint ("MCP") arthroplasty. Effective splinting of the patient's hand following such surgery is critical to a successful outcome. In order to heal properly, the reconstructed joint must be supported in the proper alignment while permitting the fingers to periodically articulate between extended and flexed positions. Since the anatomy and functional range of motion of each patient's hand is different, it is important that the splint be optimally adjusted to suit each individual. The applicant's splint 10 is specially adapted for this purpose.

Figure 1:
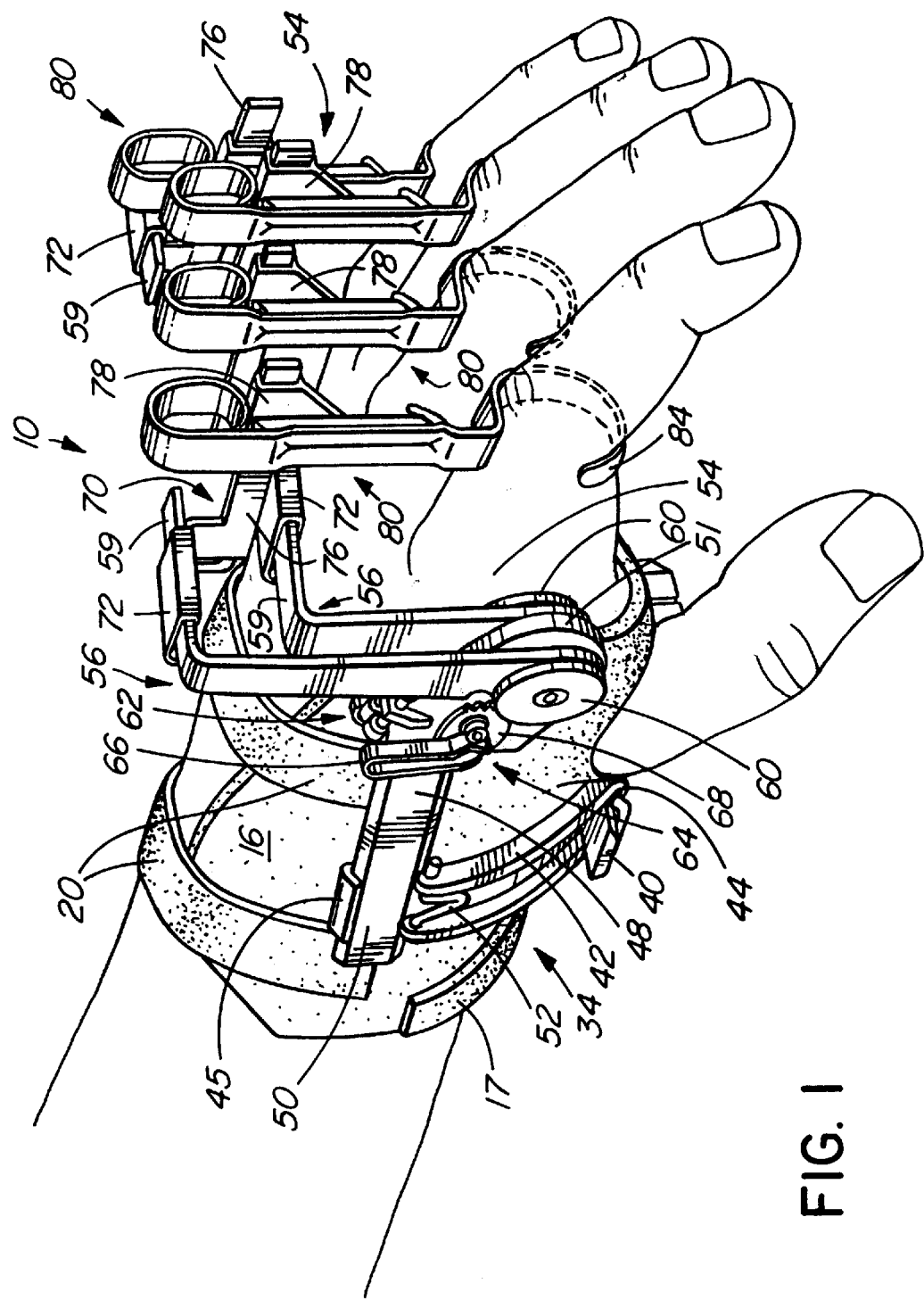
FIG. 1 is a front isometric view of the applicant's splint supporting the patient's fingers in an extended position.
Figure 2:
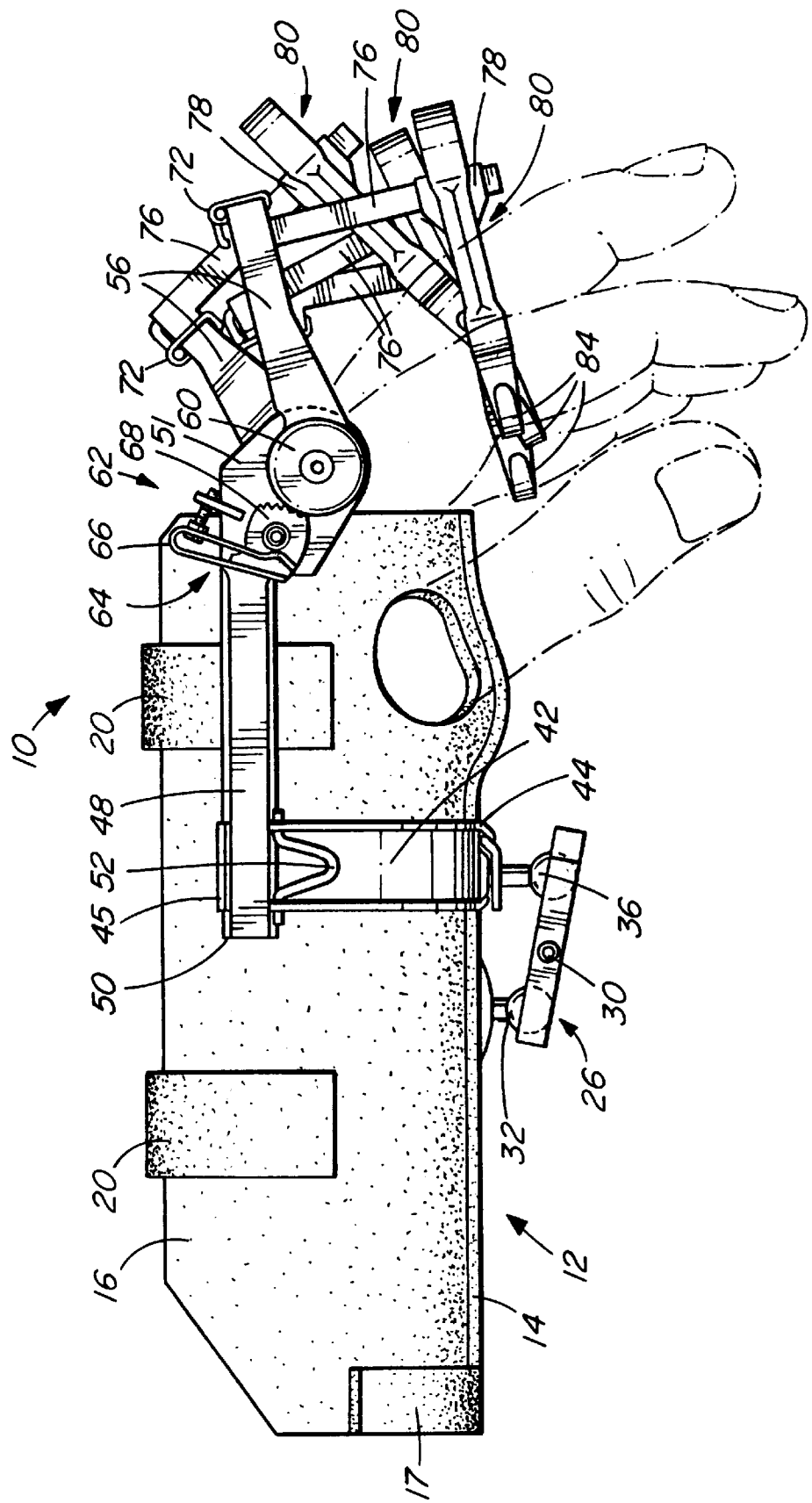
FIG. 2 is a right side elevational view of the splint of FIG. 1 showing the patient's fingers in a flexed or partially flexed position.
Figure 5:
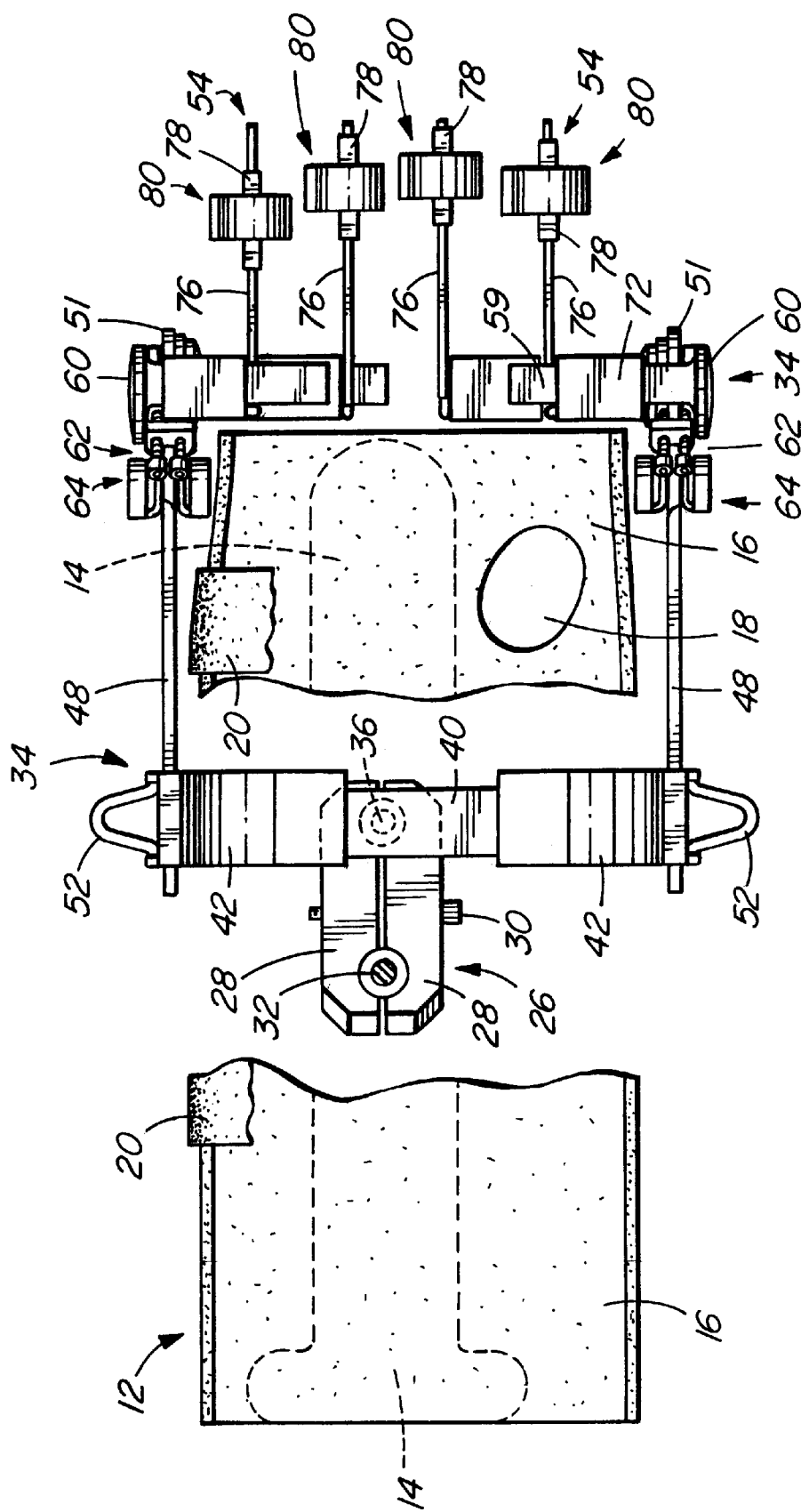
FIG. 5 is a top plan view of the splint of FIG. 1.

Splint 10 includes a brace 12 for supporting the patient's forearm. As shown best in FIGS. 5 and 6, brace 12 includes a metal stay 14, preferably made from light-weight, flexible aluminum, which is generally aligned with the patient's ulnar axis. Stay 14 fits within a sleeve formed in a central, longitudinal portion of an armlet 16. Stay 14 may be contoured to conform to the patient's forearm. For example, the forward end of stay 14 may be curved to support the patient's palm and maintain a normal hand arch. The rear end of stay 14 includes wings 17 which curve upwardly on either side of the patient's forearm. Armlet 16 is preferably made of neoprene or some other material and which will conform to the user's forearm. Armlet 16 includes an aperture 18 in the lower, forward end thereof to accommodate the patient's thumb. An extension of stay 14 may optionally be added here to support a thumb fusion. As shown in FIGS. 1 and 2, armlet 16 also includes a pair of straps 20 securable to fasteners for wrapping armlet 16 snugly around the patient's forearm. Alternative strapping arrangements may include two rows of eyelets laced together with a continuous lace which finishes in one or more pull straps. In a another alternative embodiment of the invention, brace 12 may be moulded from a thermoplastic material.

Stay 14 further includes a first ball joint coupler 32 projecting downwardly from a central portion thereof (FIG. 2). A hole (not shown) is cut in the fabric of armlet 16 to accommodate the stem of ball joint coupler 32. The rounded end of coupler 32 is captured at the rear end of a clamp 26 which extends underneath brace 12. Clamp 26 comprises matching halves 28 which are releasably coupled together with a fastener 30.

An adjustment frame generally designated 34 is pivotally coupled to a forward end of clamp 26. As shown best in FIGS. 5 and 6, frame 34 includes a transverse bar 40 having a second ball joint coupler 36 projecting downwardly from a central portion thereof. Coupler 36 has a rounded end captured by clamp 26.

Figure 3:
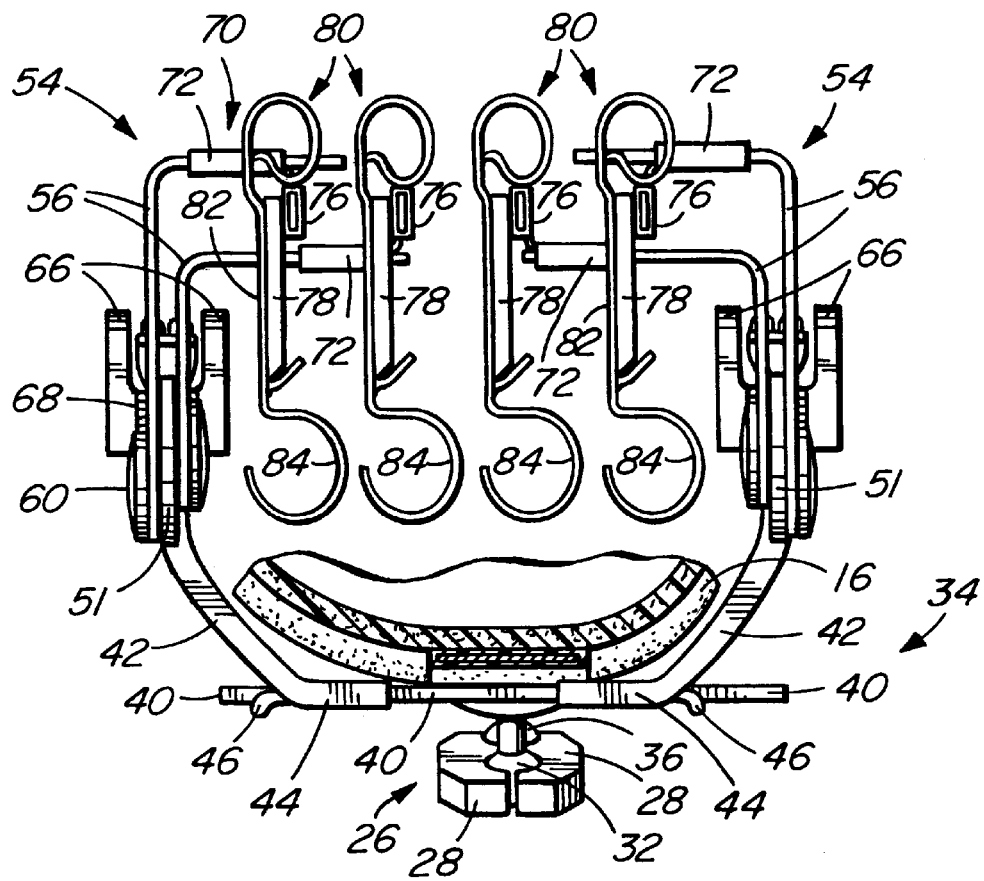
FIG. 3 is a front isometric view of the splint of FIG. 1.
Figure 4:
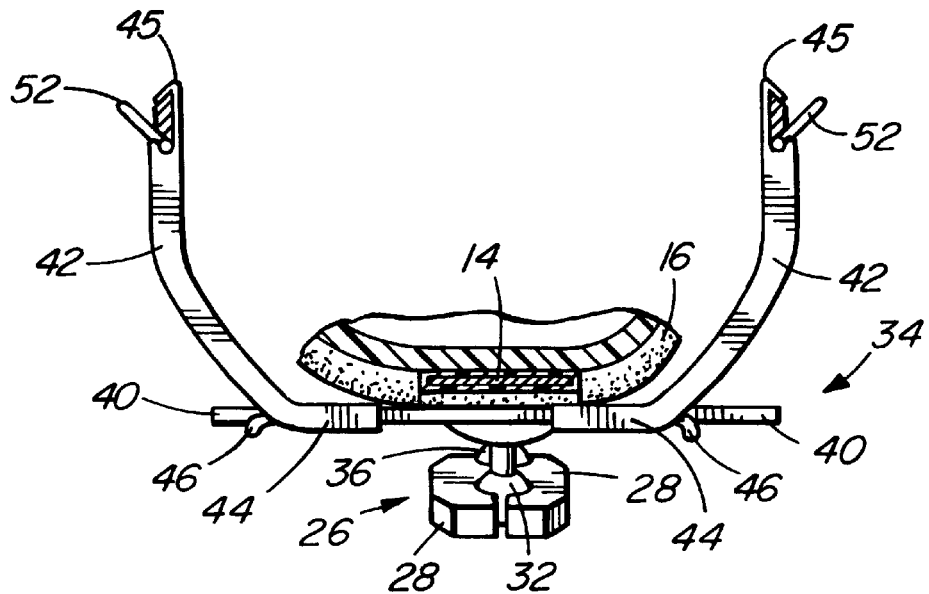
FIG. 4 is a rear isometric view of the splint of FIG. 1.
Figure 6:
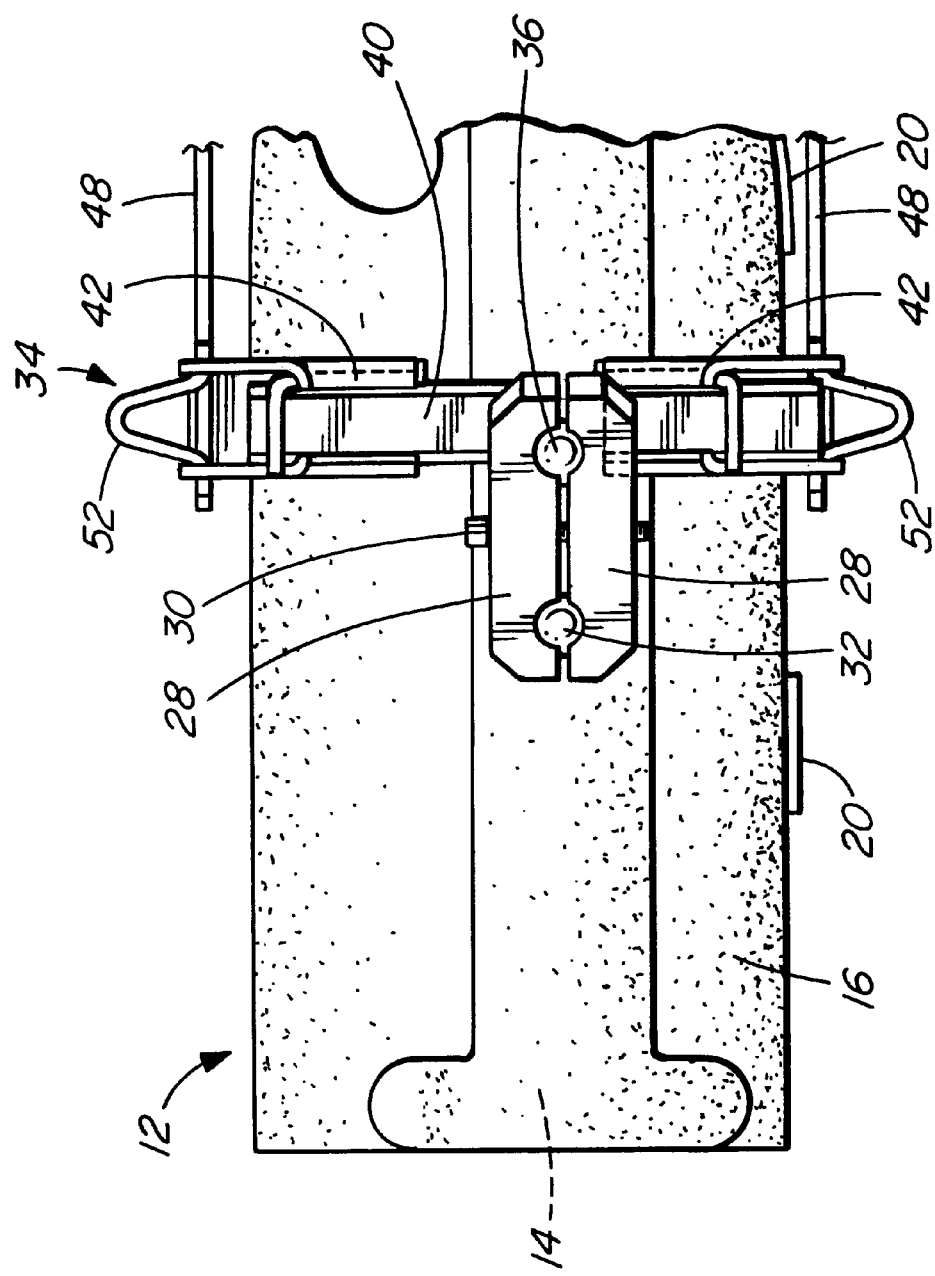
FIG. 6 is a bottom plan view of a rear portion of the splint of FIG. 1.

Adjustment frame 34 also includes a pair of side frames 42 which curve upwardly and outwardly on opposite sides of splint 10. The lower end 44 of each side frame 42 is sidably coupled to bar 40 to enable adjustment of the distance between side frames 42 to accommodate hands of varying widths. For example, each side frame 42 may comprise a slot sized to receive bar 40 (FIG. 6). Each side frame 42 may be releasably locked to bar 40 at a selected position using a first cam lock 46 (FIGS. 3 and 4).

Figure 7:
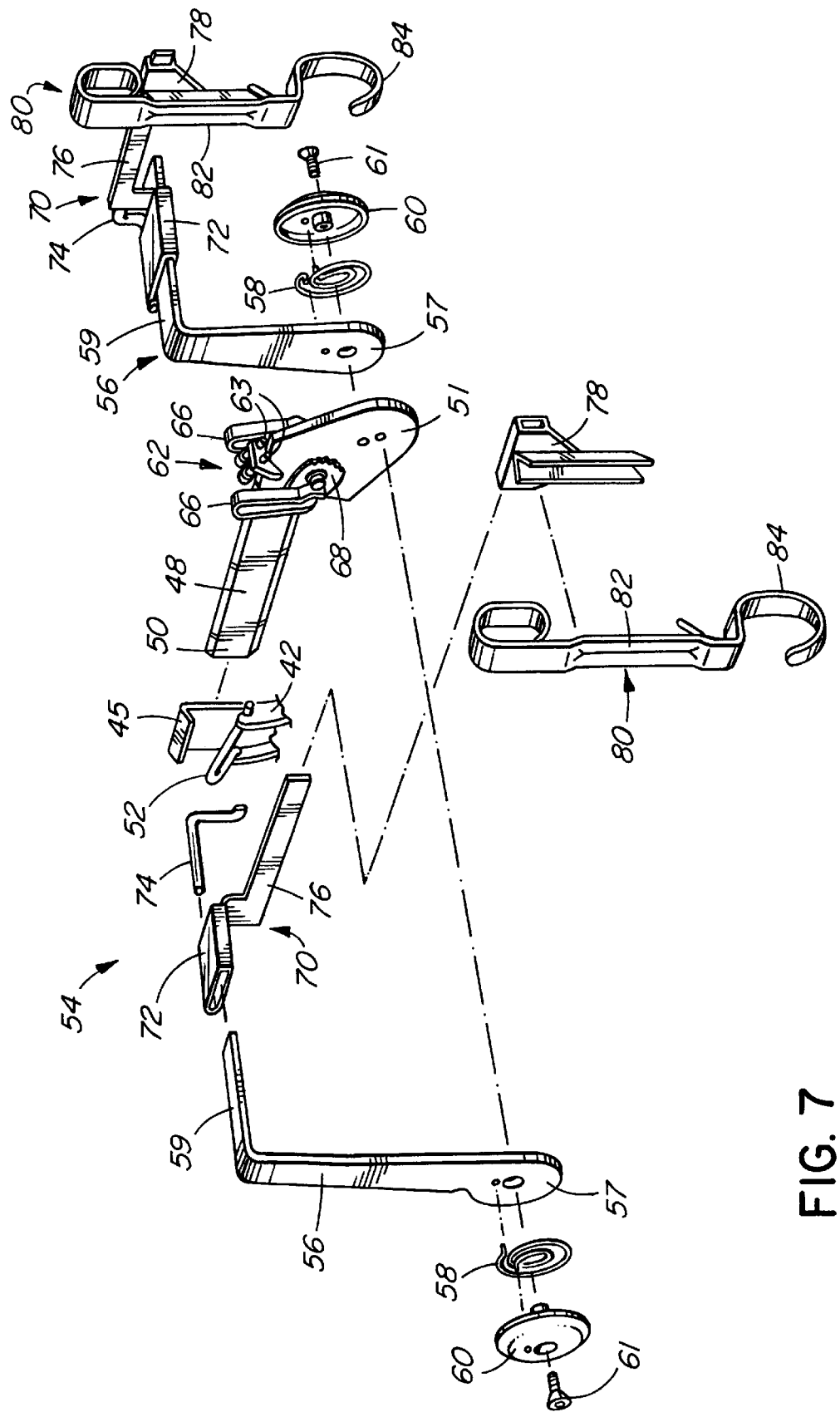
FIG. 7 is an exploded isometric view of a finger support assembly.

Adjustment frame 34 further includes a pair of side bars 48 which extend longitudinally on opposite sides of splint 10. A rear end 50 of each side bar 48 is sidably coupled to an upper end 45 of a respective side frame 42. For example, side frame upper end 45 may comprise a slot sized to receive side bar 48 (FIG. 7). A second cam lock 52 is provided to releasably lock side bar 48 at a selected longitudinal position.

Splint 10 further includes a pair of finger support assemblies 54 which are each pivotally coupled to adjustment frame 34. As shown best in FIG. 7, each assembly 54 comprises a pair of L-shaped rigging arms 56 each having a rounded end 57 pivotally coupled to an enlarged forward end 51 of a respective side bar 48. Each rigging arm 56 is coupled to either an inner or an outer surface of side bar 48 with fasteners 61 together with an extension assist spiral torsion spring 58 and a spring retainer cap 60. Spiral torsion spring 58 has an end which fits into a corresponding hole formed in side bar end 51 and is tensioned when the corresponding rigging arm 56 is pivoted forwardly to a flexed position as discussed further below. Thus, spring 58 biases a respective rigging arm 56 to a vertical orientation shown in FIG. 1 for supporting the patient's MCP joints in an extended position. In one embodiment of the invention, the tension of springs 58 is adjustable to provide greater or lesser resistance to flexion.

A stop 62 is mounted on each side bar 48 for restricting rearward pivoting motion of rigging arms 56 beyond the vertical orientation of FIG. 1, thereby preventing hyper-extension of the patient's MCP joints. Each stop 62 may consist of an extension governor screw 63 rotatable to adjust the extension limit of a corresponding rigging arm 56.

Each rigging arm 56 is bent at an elbow to provide a mounting platform 59 which extends over the patient's hand toward the mid-line of splint 10. The inner rigging arm 56 of each finger support assembly 54 is shorter in height and has a longer mounting platform 59 than the adjacent outer rigging arm 56 (FIGS. 1 and 3). As discussed further below, this ensures that the path of the inner rigging arm 56 will not be obstructed by the adjacent outer rigging arm 56 when the finger support assembly 54 is articulated to a flexed position.

A pair of spring-loaded flexion locks 64 each having a handle 66 and a stop 68 are provided to lock each pair of rigging arms 56 in a selected flexed position against the bias of springs 58. As shown best in FIG. 2, when each lock 64 is deployed, a serrated edge of stop 68 engages the rounded end 57 of a corresponding rigging arm 56 to restrict pivoting motion thereof. Flexion locks 64 restrict extension only, as the serrations are so designed to allow the rigging arm to follow the finger as it moves into flexion. Lock 64 may be disengaged by pushing lock handle 66 rearwardly to the unlocked position of FIG. 1, thereby allowing rigging arms 56 to pivot freely. The bias of extension assist spiral torsion springs 58 returns the rigging arms to the extended position of FIG. 1, thereby applying a small extension force to each finger.

As shown best in FIG. 7, each finger support assembly 54 further includes a pair of spars 70 which are sidable transversely along a mounting platform 59 of a respective rigging arm 56. Each spar 70 has a sleeve 72 for receiving a mounting platform 59. Each spar sleeve 72 may be locked at a selected transverse position by means of a third cam lock 74.

Each spar 70 also includes an elongate member 76 extending forwardly from sleeve 72 parallel to the longitudinal axis of splint 10. In the extended position of FIGS. 1 and 3, the elongate members 76 of splint 10 preferably extend in a common horizontal plane. Since mounting platforms 59 of rigging arms 56 are staggered at different elevations, the orientation of spars 70 is adjusted accordingly (i.e. spar sleeves 72 connected to the outer rigging arms 56 extend downwardly whereas spar sleeves 72 connected to the inner rigging arms 56 extend upwardly).

A sling holder 78 is sidable along the length of each member 76 for detachably supporting a respective sling 80. Sling 80 has an upper portion 82 which is securable to holder 78 and a C-shaped lower portion 84 for supporting a finger of the patient (FIGS. 1 and 2). Slings 80 may be of the same or varying lengths to suit the requirements of the patient. In one embodiment, the sling upper portion may comprise a leaf spring which releasably snaps into place on a respective sling holder 78 as shown best in FIG. 7. An alternative design (not shown) for sling holder 78 will include a lockable sliding joint (i.e. a fourth cam lock).

As should be apparent from FIG. 1, splint 10 ordinarily consists of two finger support assemblies 54 mounted on opposite sides of splint 10, each supporting two adjacent fingers of the patient. Each assembly 54 is a structurally identical, mirror-image of the opposite assembly. MCP joint arthroplasty typically involves the reconstruction of all of the MCP joints of a patient's hand. However, if only one or two of the finger joints are fitted with a prosthesis, then only one finger support assembly 54 would be required.

Splint 10 is essentially bilaterally symmetrical and may be used on either a left or right hand with relatively few modifications. The embodiment shown in the drawings is adapted for right-hand use. In the case of left-hand use, thumb aperture 18 formed in armlet 16 (FIG. 5) is located on the opposite side of splint 10.

In use, splint 10 may be quickly and precisely adjusted to suit the hand anatomy of a particular patient. Splint 10 is preferably provided to therapists fully assembled. In order to fit a particular patient, the armlet 16 is first detached from frame 34 by loosening ball joint clamp 26. The aluminum stay 14 within armlet 16 is bent to fit the patient's palmer arch, forearm diameter and wrist extension. In some cases it is necessary to trim excess fabric from armlet 16 and enlarge thumb aperture 18. Straps 20, or alternative lace style straps, are then adjusted to secure armlet 16 snugly to the patient's forearm.

The therapist then removes finger slings 80 from their respective sling holders 78. Sling holders 80 are positioned for right or left hand use. The spacing between opposed side frames 42, which are slidable on bar 40, is temporarily preset at an excess width. The armlet 16 is pivotably reconnected to frame 34 by tightening ball joint clamp 26. Clamp 26 is sufficiently tightened to allow pivoting of ball joints 32, 36 upon the application of a moderate force (clamp 26 is fully tightened after correct alignment has been obtained).

The next step in the fitting procedure is for the therapist to adjust side frames 42, side bars 48 and ball joints 32, 36 repeatedly as described above until the pivot axis passing through all four rigging arms 56 is approximately in line with the mean axis through the patient's MCP joints. In practice, this pivot axis should be set slightly higher than the axis of the patient's relaxed hand to compensate for upwardly directed extension forces applied to the patient's fingers when they are fitted into splint 10 as described below. It is important that the left and right side bars 48 be in approximately the same position relative to their respective side frames 42. If the alignment is only acceptable on one side of splint 10, then it may be necessary to further adjust ball joints 32 and 36.

Finger slings 80 are sized to fit the patient's fingers. The lower portion 84 of each sling 80 holds a respective finger on the ulnar side. Sling lower portion 84 supports the finger in extension and positions the finger in flexion. There must be adequate finger clearance for comfort and easy access. Once the necessary adjustments have been made, each finger sling 80 is then snapped into place on a respective sling holder 78.

The preferred position of the finger sling 80 depends upon which of the patient's finger joints have been fitted with a prosthesis. In the case of MCP joint arthroplasty, the finger sling 80 is typically fitted on the shaft of the proximal phalanx as close to the proximal interphalangeal joint as comfort allows, as shown best in FIG. 1. This allows for flexion of the proximal and distal phalangeal joints so that the patient can maintain a relatively normal range of motion in the end portions of his or her fingers while wearing splint 10. In the case of proximal interphalangeal and distal interphalangeal arthroplasty, finger slings 80 may be positioned at any other suitable position on the patient's finger and the MCP joints would need to be stabilized. The longitudinal position of the finger sling 80 may be adjusted by sliding a sling holder 78 along the length of a respective spar 70. The transverse position of the finger sling 80 may be adjusted by sliding the spar 70 along the length of a respective rigging arm 56 and locking it in place at the desired position with a third cam lock 74.

As discussed above, an important feature of the applicant's invention is that the height, inclination, width and length of adjustment frame 34 may be independently varied to ensure that the pivot axis of rigging arms 56 approximates the natural pivot axis of the finger joints in question. The height and inclination of adjustment frame 34 may be modified by pivoting transverse bar 40 relative to clamp 26 about ball joint coupler 36; and by pivoting clamp 26 about coupler 32 relative to stay 14 (FIG. 2). The width adjustment is achieved by sliding side frames 42 transversely along the length of bar 40 and locking the side bars 48 in place at the desired position with first cam locks 46. The longitudinal adjustment is achieved by sliding side bars 48 forwardly or rearwardly relative to side frames 42 and locking them in the desired position with second cam locks 52. Unlike some prior art designs, all adjustments may be made while splint 10 is worn by the patient, ensuring a more accurate fit.

As indicated above, frame 34 is preferably adjusted so that the pivot axis of rigging arms 56 (i.e. the transverse axis passing through fasteners 61 as shown in FIG. 7) very closely approximates the natural pivot axis of the finger joint fitted with a prosthetic implant. This ensures that the joint will move through a natural range of motion when splint 10 is adjusted between extended and flexed or semi-flexed positions. By ensuring that the joint is fully supported but may move through a natural range of motion, splint 10 helps minimize the unwanted radial, protractive and retractive forces to the joint which are commonplace in conventional splints and which may disrupt the post-operative healing process.

Movement of the patient's fingers between extension (FIG. 1) and flexion (FIG. 2) is critical to successful recovery. Splint 10 is designed to support each finger while it moves between extension and flexion. Spiral torsion spring 58 provides assistance for weak extensor muscles when movement is from flexion to extension. When a passive flexion force is desired each rigging arm 56 is pivoted downwardly and a corresponding flexion lock 64 is engaged as discussed above to lock the rigging arm 56 in place. When the flexion locks 64 are disengaged, springs 58 assist in returning the patient's fingers to a fully extended position. As discussed above, the elevation of the rigging arms 56 is staggered so that an inner arm will not obstruct pivoting motion of an adjacent outer arm, or vice versa, when the rigging arms are moved between the extended and flexed positions.

Since splint 10 is pre-assembled and each setting of adjustment frame 34 is independently adjustable, splint 10 may be quickly and precisely adjusted or readjusted to suit the needs of a particular patient, or to fit on to a new patient. Prior art splints typically require a very high degree of time-consuming custom fitting and suffer from the drawback that a change in one setting (for example, the position of an elastic finger sling) necessitates a change in many other interrelated settings of the splint (for example, the position of an outrigger platform).

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

What is claimed is:

1. A splint for post-operative treatment of at least one surgically repaired joint of a patient's fingers, the repaired joint being located at the union between two finger bones and having a natural pivot axis about which the bones move relative to one another when in anatomically correct alignment, said splint comprising:
   (a) a brace securable to a forearm of the patient;
   (b) at least one finger support for engaging a finger of the patient containing the repaired joint, wherein said finger support is moveable about a support pivot axis to permit movement of the finger between extended and flexed positions; and
   (c) an adjustment frame coupling said finger support to said brace for adjusting the position of said support pivot axis until it is substantially coaxial with the natural pivot axis of the repaired joint.

2. The splint of claim 1, wherein the width, height and length of said adjustment frame are independently adjustable.

3. The splint of claim 1, wherein said adjustment frame is pivotally coupled to said brace.

4. The splint of claim 1, wherein said adjustment frame further comprises:
   (a) a rod pivotally coupled to said brace and extending transversely between opposite sides of said splint; and
   (b) at least one side frame sidably coupled to said rod and lockable at a selected transverse position thereon.

5. The splint of claim 4, wherein said adjustment frame further comprises at least one side bar extending longitudinally alongside the patient's hand which is slidably coupled to said side frame and is lockable at a selected longitudinal position.

6. The splint of claim 4, wherein said rod is pivotally coupled to an undersurface of said brace and extends underneath said brace.

7. The splint of claim 6, wherein said adjustment frame comprises a pair of side frames, each side frame extending upwardly and outwardly from said rod to a respective side of said splint.

8. The splint of claim 7, wherein said adjustment frame comprises a pair of side bars, wherein each side bar is slidably coupled to an upper end of a respective side frame.

9. The splint of claim 8, comprising a pair of said finger supports, wherein each finger support is pivotally coupled to a forward end of one of said side bars.

10. The splint of claim 9, wherein each said finger support is an assembly comprising:
    (a) a rigging arm pivotally coupled to said side arm and extending inwardly therefrom above the finger in said extended position; and
    (b) a sling adjustably connectable to said rigging arm for supporting the finger.

11. The splint of claim 10, wherein said finger support further comprises:
    (a) a spar slidable transversely on said rigging arm and lockable at a selected transverse position, said spar having a support rod which extends longitudinally; and
    (b) a sling holder slidable longitudinally on said spar, wherein said sling is detachably connectable to said spar.

12. The splint as defined in claim 11, wherein each finger support comprises a pair of said rigging arms independently pivotable relative to said side bar, wherein said rigging arms extend at different elevations above the hand of the patient in said extended position.

13. The splint as defined in claim 12, wherein said adjustment frame further comprises a plurality of flexion locks, wherein each of said locks releasably maintains one of said rigging arms at a selected angular position between said extended and flexed positions.

14. The splint of claim 1, wherein said brace comprises:
   (a) an elongated stay conformable to the contour of the patient's forearm; and
   (b) a flexible armlet receiving said stay and releasably fastenable around the patient's forearm.

15. The splint of claim 1, wherein said finger support is pivotally coupled to a forward end of said adjustment frame.

16. The splint of claim 1, wherein said finger support is biased toward said extended position.

17. The splint of claim 16, wherein said adjustment frame further comprises a flexion lock for releasably locking said finger support at a selected angular position between said extended and flexed positions.

18. The splint of claim 17, further comprising an adjustable stop for restraining rearward pivoting motion of said finger support in said extended position.

19. The splint as defined in claim 1, further comprising a clamp extending underneath said brace, wherein said brace and said adjustment frame are independently pivotally connected to said clamp by first and second ball joint connectors.

20. A splint for post-operative treatment of a patient following metacarpophalangeal joint arthroplasty, the metacarpophalangeal joint being located at the union of two finger bones and having a natural pivot axis about which the bones move relative to one another when in anatomically correct alignment, said splint comprising:
   (a) a brace secureable to a forearm of the patient;
   (b) a finger support for engaging at least one finger of the patient near the patient's metacarpophalangeal joint, wherein said finger support is moveable about a support pivot axis to permit movement of the finger between extended and flexed positions; and
   (c) an adjustment frame coupling said finger support to said brace for adjusting the position of said support pivot axis until it is approximately aligned coaxial with the natural pivot axis of the metacarpophalangeal joint.

21. A splint for dynamically supporting at least one finger joint of a patient, the finger joint being located at the union between two finger bones and having a natural pivot axis about which the bones move relative to one another when in anatomically correct alignment, said splint comprising:
   (a) a brace securable to a forearm of the patient;
   (b) at least one finger support for engaging a finger of the patient containing the finger joint, wherein said finger support is moveable about a support pivot axis to permit movement of the finger between extended and flexed positions; and
   (c) an adjustment frame coupling said finger support to said brace for adjusting the position of said support pivot axis until it is substantially coaxial with the natural pivot axis of the finger joint.

22. The splint as defined in claim 21, further comprising biasing means for biasing said finger support toward said extended position, wherein said biasing means applies a biasing force to the patient's finger bones in a direction substantially perpendicular to the longitudinal axis thereof throughout the range of motion of the patient's finger between the extended and flexed positions.

23. The splint as defined in claim 21, wherein said splint comprises first, second, third and fourth finger supports, each of said finger supports for supporting one of the patient's fingers, wherein each of said first, second, third and fourth finger supports is pivotably coupled to said adjustment frame and is independently moveable relative thereto.

24. A hand splint for wear by a patient comprising:
   (a) a brace securable to a forearm of the patient;
   (b) at least one finger support for engaging a finger of the patient, wherein said finger support is moveable about a support pivot axis to permit movement of the patient's finger between extended and flexed positions; and
   (c) an adjustment frame coupling said finger support to said brace for adjusting the position of said support pivot axis, wherein said adjustment frame comprises a rod pivotally coupled to the brace and extending transversely between opposite sides of said splint and at least one side frame slidably coupled to said rod and lockable at a selected transverse position.

25. The hand splint as defined in claim 24, wherein said adjustment frame further comprises at least one side bar extending longitudinally alongside the patient's hand which is slidably coupled to said side frame and is lockable at a selected longitudinal position, wherein said at least one finger support is pivotally coupled to said side bar.

* * * * *